United States Patent [19]

Wagenknecht et al.

[11] Patent Number: 4,850,981
[45] Date of Patent: Jul. 25, 1989

[54] ARENTERAL INFUSION OF NITROGLYCERIN SOLUTIONS

[75] Inventors: Dietmar M. Wagenknecht, Zion; Anton H. Amann, Libertyville, both of Ill.; Daphne R. Gallagher, Fountain Valley, Calif.

[73] Assignee: E. I. Du Pont de Nemours and Company, Wilmington, Del.

[21] Appl. No.: 460,616

[22] Filed: Jan. 24, 1983

Related U.S. Application Data

[63] Continuation of Ser. No. 65,433, Aug. 10, 1979, abandoned.

[51] Int. Cl.⁴ ............................................. A61M 5/14
[52] U.S. Cl. ..................................... 604/251; 604/407
[58] Field of Search .................... 526/352; 128/214 F, 128/214 R; 210/500.2, 927; 424/426; 604/251, 407

[56] References Cited

U.S. PATENT DOCUMENTS 3,298,367  1/1967  Bergman .............................. 128/214

OTHER PUBLICATIONS

Edelman, et al., "The Stability of Hypodermic . . . Dispensing Container", T. of The Amer. Pharmaceutical Assoc., 1971 NS11(1), Copy in 210-927.
Cossum et al., The Lancelet, Aug. 12, 1978, pp. 349 and 350.
Markson Science Supplies, 1978-79 Catalog, Markson Science Inc., pp. 228, 229, 232 and 233.
Brydson, Plastics Materials, London, ILIFFE Books Ltd., 1966, 98 Through 118.

*Primary Examiner*—Frank Spear
*Attorney, Agent, or Firm*—Gildo E. Fato; Donald L. Barbeau

[57] ABSTRACT

Intravenous infusion sets suitable for the parenteral administration of nitroglycerin solutions and methods of using such sets are provided. The intravenous infusion sets and methods herein utilize flexible drip tubes having their inner surfaces constructed of polyolefin plastic material. Polyolefin or polyolefin-lined drip tubes can be advantageously used to infuse nitroglycerin solutions with minimized loss of nitroglycerin solution potency.

19 Claims, No Drawings

ARENTERAL INFUSION OF NITROGLYCERIN SOLUTIONS

This is a continuation of application Ser. No. 065,433, filed Aug. 10, 1979, now abandoned.

The present invention relates to an improved intravenous (IV) infusion set which is especially suitable for parenterally administering nitroglycerin solutions to patients in need of such treatment. An improved method for parenterally administering nitroglycerin is also provided.

Nitroglycerin is a vasodilator which is utilized in the treatment of myocardial infarct patients. Frequently this drug is administered orally, but in acute myocardial infarct cases, nitroglycerin can be parenterally administered in an attempt to reduce the size of the infarct.

Nitroglycerin is a potent drug, and its accurate titration during parenteral infusion is quite important. When infusing nitroglycerin solutions through conventional, commercially-marketed IV infusion sets, however, it has been observed that, during passage of the parenteral liquid through the plastic drip tubing, the potency of the nitroglycerin solution is lowered. Thus, the precise amount of drug administered to the patient through such IV sets is unknown even though the amount of solution administered is known. Without being bound by any particular theory, it is believed that nitroglycerin is adsorbed by the inner surfaces of the plastic tubing used in conventional IV sets, thereby resulting in a flow-rate dependent loss of nitroglycerin from solutions passing through the tubing.

Given the importance of parenterally administering precise amounts of nitroglycerin to myocardial infarct patients, it is an object of the present invention to provide intravenous infusion apparatus and methods which are especially suitable for parenterally administering nitroglycerin solutions with minimized loss of nitroglycerin potency.

In its article aspect, the present invention involves an intravenous infusion set which can be used for the accurate parenteral administration of nitroglycerin solutions. Such infusion sets generally comprise a reservoir for holding a supply of nitroglycerin-containing parenteral liquid to be infused and a flexible drip tube connecting this reservoir to an administration needle suitable for insertion into the patient's vein. The drip tube contains some means for controlling flow of liquid from the reservoir through the tube. The drip tube will also frequently contain means for monitoring or measuring such liquid flow.

The reservoir of the intravenous infusion set of the present invention contains the nitroglycerin solution to be parenterally administered. Such a reservoir is generally provided in a container, e.g., a bottle or bag, which can be suspended several feet above the patient in order to provide hydrostatic pressure sufficient to force the nitroglycerin solution through the drip tube and administration needle and into the patient's vein. The shape, configuration and construction of the reservoir container is not critical, and any suitable conventional bag or bottle may be employed. Containers for nitroglycerin-containing parenteral liquids include, for example, those described in McPhee; U.S. Pat. No. 3,921,630, issued Nov. 25, 1975, incorporated herein by reference. Preferably the container for the reservoir of nitroglycerin solution is constructed of a material, e.g. glass or polyolefin, which does not promote the adsorption of nitroglycerin to the container surface.

The nitroglycerin solution which serves as the parenteral liquid suitable for infusion through the IV set of the present invention generally contains from about 50 $\mu g/ml$ to 250 $\mu g/ml$ of nitroglycerin, preferably from about 75 $\mu g/ml$ to 150 $\mu g/ml$ nitroglycerin. Such solutions are aqueous and frequently also contain dextrose, lactose, sodium chloride or other materials conventionally administered in parenteral liquids. Nitroglycerin for use in preparing the parenteral liquid for infusion is commercially available in ampules, for example 10 ml ampules containing 0.5 mg/ml of nitroglycerin. Nitroglycerin in this form can be diluted to the desired concentration for administration by admixing the contents of such ampules with commercially available Sodium Chloride Injection or Dextrose Injection products.

The flexible drip tube in the IV set herein connects the nitroglycerin solution reservoir to the parenteral liquid administration needle. Such tubes generally range from about 15 to 100 inches in length and have inside diameters sufficient to permit a flow rate of from about 0.2 milliliters per minute to 2.0 milliliters per minute, preferably 0.5 milliliters per minute to 1.5 milliliters per minute, of nitroglycerin solution to pass through the tube. Advantageously the inside diameter of such tubing ranges from about 0.15 mm to about 6 mm.

In accordance with the present invention, the inside surface of the drip tube is constructed essentially of a polyolefin plastic material. It has been surprisingly discovered that such a polyolefin inner surface in the tube permits nitroglycerin solution to flow through the drip tube with minimized loss of nitroglycerin concentration in the parenteral solution administered. Unlike conventional tubing materials such as polyurethane, polyvinylchloride and polyethylvinyl alcohol, tubing with a polyolefin inside surface does not adsorb nitroglycerin to such an extent that nitroglycerin concentration in the liquid being transmitted is lowered to an unacceptable degree.

The olefin polymers which may be employed for the inner surface of the drip tube herein include the normally solid, higher molecular weight polymers of ethylene, propylene and higher molecular weight olefins. The most common materials of this type include high pressure (low and intermediate density) polyethylene, high-density polyethylene, Ziegler or low pressure process polyethylene and polypropylene.

Preferred polyolefins for use in the invention herein have molecular weights ranging from about 1,500 to 150,000 or more, preferably from about 20,000 to 100,000. Low and intermediate density polyethylenes, produced by the high pressure polymerization of ethylene, conventionally range in density from about 0.91 to 0.94 grams per cubic centimeter. High density polyethylene, produced by the low pressure polymerization of ethylene, e.g., by the Ziegler process, conventionally range in density from about 0.93 to 0.97 grams per cubic centimeter. Polypropylene, in its isotactic, syndiotactic or atactic forms and having a density of about 0.85 to 0.90 grams per cubic centimeter, can also be advantageously employed for the drip tube inside surface in the present invention. Polyolefins of the type contemplated for use herein are more fully described in Kirk-Othmer, *Encyclopedia of Chemical Technology, Vol. 14, 2nd Edition,* "Olefin Polymers", pages 217–313 (Interscience Publishers, 1967). which article is incorporated herein by reference.

Tubing constructed essentially entirely of polyolefin plastic material is advantageously employed as the drip tube in the IV sets and methods of the present invention. Tubing of this type is commercially available in a variety of sizes and forms. Polyethylene tubing, for example, is commercially available from Matrek Medical Products and under the "CLAY ADAMS" tradename from Markson Science, Inc. Alternatively, tubing constructed from non-polyolefin material, e.g., various plastic materials, but which utilizes an inside lining of polyolefin may also be advantageously employed in the present invention. Polyethylene-lined tubing of this type is also commercially available, for example, under the tradename "BEV-A-LINE", marketed by Thermoplastic Scientifics, Inc. and also marketed by Markson Science Inc.

The flexible drip tube flow path of the IV infusion set herein will frequently contain conventional means for controlling and conventional means for monitoring or measuring flow of the nitroglycerin solution from the reservoir through the drip tube to the vein. Means for controlling parenteral solution flow can include various types of devices such as manual or electronic pinch valves or roller clamps. A capillary flow controlling device such as that described in Bergman; U.S. Pat. No. 3,298,367, issued Jan. 17, 1967, may also be advantageously employed. When the flow control means operates by pinching or squeezing the flexible drip tube, the lined polyethylene tubing described above is especially useful. Such tubing has a requisite flexibility characteristic for use with such pinching or squeezing devices. Means for measuring or monitoring flow of the nitroglycerin solution may also be provided. Such monitoring/measuring means can be provided, for example, by a transparent drip chamber through which drops of parenteral fluid flowing from the nitroglycerin solution reservoir can be counted. A rotometer may also be employed to indicate drip rate. Both the flow control means and the flow measuring/monitoring means are, of course, placed within the flow path of the drip tube and are positioned between the nitroglycerin solution reservoir and the parenteral administration needle.

Advantageously, the intravenous infusion sets of the present invention are sold as packages, each of which packages comprises the flexible drip tube, administration needle and flow control means as herebefore described along with one or more nitroglycerin ampules for use in preparing the nitroglycerin-containing parenteral liquid to be infused through the IV set.

In its method aspect, the present invention relates to a method of parenterally administering a nitroglycerin solution to a patient with minimized loss of nitroglycerin potency during such administration. Such a method comprises passing the nitroglycerin solution described above through a flexible drip tube to an intravenous administration needle for infusion. The flexible drip tube so employed has its inner surfaces constructed of a polyolefin plastic material as hereinbefore described, which material minimizes adsorption of nitroglycerin from the nitroglycerin solution passing through the tube.

The problem of nitroglycerin loss during IV infusion as well as the intravenous infusion set and the intravenous infusion method of the present invention are illustrated by the following examples which are not limiting of the invention herein.

EXAMPLE I

Nitroglycerin Loss Through Commercial IV Sets

Loss of nitroglycerin solution potency as a function of time is determined for nitroglycerin solutions delivered through eight commercially-available IV sets. The IV sets tested are described in Table 1.

TABLE I

Commercially-Available IV Sets

A. Travenol Minidrip Solution Administration Set
   Lot H259R9, 60 gtts./ml., 70" long.
B. McGaw Pediatric AdditIV ® Set, 60 gtts./ml., 96" long
   Lots V1449F7P068.
C. Cutter Saftiset ® Intralipid Administration Set
   808-05
   Lot B4083, 60 gtts./ml., 92" long.
D. Abbott Twin-Site ® Venoset ® with Cair TM Clamp
   Lot 86-239-DT, 15 gtts./ml., 103" long.
E. Baxter Administration Set for I.V. Fluids Code
   FKC0037
   (Baxter Div., Travenol Labs, Ltd., Thetford
   Norfolk, England)
   Lot K117C746, dated 11/16/77, 15 gtts./ml.,
   61" long.
F. Avon Blood Administration Set A10
   (Avon Medicals Ltd., Birmingham B30, 3DR England)
   Batch #758YG, Sterilized 7/72, 15 gtts./ml.,
   70" long.
G. Avon Blood Administration Set A11
   (Avon Medicals Ltd., England)
   Batch #078 M G5, Sterilized 12/75, 1t gtts./ml.,
   70" long.
H. Intrafix ® Air Infusion Set
   B. Braun Melsungen AG, W. Germany 17077K1522
   402
   approx. 60" long.

A test solution containing 100 μg/ml of nitroglycerin in Sodium Chloride Injection, USP IV fluid is tested in each set. Such a solution is prepared from a commercial nitroglycerin solution (10% on lactose) by diluting 50 ml of such a nitroglycerin solution (0.5 mg/ml) to 250 ml with the IV fluid. To approximate this as closely as possible, 50 ml of the sodium chloride injection is first withdrawn by syringe from each new I.V. bottle and discarded. The 50 ml of nitroglycerin solution is then added by syringe to each bottle and mixed thoroughly.

In the experiments with sets A, E, F, G, and H, a control sample of the admixture is taken from the bottle prior to administration set attachment. Samples for sets B and C are taken from the bottles after the set is run. Samples for set D are taken from the bottles before and after the set is run. Once admixtures are completed (and samples taken), each administration set is inserted into the I.V. bottle according to package instructions. The bottle is inverted and hung, and the set is filled. Once filled, each set is regulated at a drip rate which would deliver approximately 1 ml/minute. Certain administration sets are more difficult to regulate than others and the necessity of frequent adjustments varies among them.

Once regulated properly, an initial sample is taken over three minutes from each set. For sets A and B, this sample is taken during the first three timed minutes. For sets C, D, E, F, G, and H, this first sample is taken for one and one-half minutes prior to starting the timer and continued one and one-half minutes beyond the start of the timer. The total is then three minutes (and theoretically 3 ml) with an "average" sample time of zero. Sampling for all sets proceeds in this manner according to the Table 2 chart below.

TABLE 2

Nitroglycerin Sampling

| Sample | Time Taken |
| --- | --- |
| 10 minutes | 8.5–11.5 minutes |
| 20 minutes | 18.5–21.5 minutes |
| 30 minutes | 28.5–31.5 minutes |
| 45 minutes | 43.5–46.5 minutes |
| 60 minutes | 58.5–61.5 minutes |
| 120 minutes | 118.5–121.5 minutes |

The samples so taken are submitted for assay along with controls prepared as herewith described. Samples which are not assayed the day of the experiment are stored at 4° C. for testing the following day.

Using the following equipment and reagents, nitroglycerin potency assay is undertaken for the samples collected:

1. Series 2 Liquid Chromatograph equipped with a Rheodyne 7105 Septumless Injector and an LC-55 Variable Wavelength Detector from Perkin-Elmer Corporation, Norwalk, CN.
2. u-Bondapak alkyl Phenyl 30 cm × 3.9 mm column from Waters Associates, Misford, MA.
3. Mobile Phase: Acetonitrile (Burdick and Jackson, Muskegon, MI)-260 Tetrahydrofuran (Burdick and Jackson, Muskegon, MI)-100
4. Trimethylchlorosilane, Pierce Chemical Co., Rockford, IL.
5. Toluene, Burdick and Jackson, Muskegon, MI.
6. Methanol, AR, Mallinckrodt, St. Louis, MO.
7. Nitric Acid, AR, Mallinckrodt, St. Louis, MO.
8. Nitroglycerin (10% on Lactose), ICI, Wilmington, DE.
9. Isosorbide Dinitrate (25% on Lactose), Napp Chemicals, Inc. Lodi, NJ.

Standard solutions for use in the analysis of the samples for the IV sets are prepared as follows: An accurately weighed sample of nitroglycerin (10% on lactose) equivalent to 100 mg. active ingredient is placed in a 100 ml. volumetric flask, and dissolved in 20 ml. Alcohol, USP and brought to volume with water. Standards of exactly 100.0, 75.0, 50.0 and 25.0 μg/ml are prepared by dilution with water. An internal standard solution is also prepared in a similar manner using an accurately weighed sample of isosorbide dinitrate (25% on lactose) equivalent to 50 mg. active ingredient and a final volume of 100.0 ml.

Using the samples from the IV sets and the standards prepared as described, the nitroglycerin potency of each sample is determined as follows: To one ml. of sample or standard in an autosampler vial is added 100 μl of internal standard solution. The vial is sealed and vortexed for 10 seconds. One hundred microliters of each sample are then injected into the Liquid Chromatograph. The mobile phase is pumped at exactly 2 ml/min., the analytical wave length is 218 nm and the sensitivity is 0.013 Absorbance Units Full Scale (AUFS). Each sample is assayed in duplicate.

The peak height ratios (nitroglycerin/isosorbide dinitrate) of the standards are used to construct a calibration curve which is employed to calculate the nitroglycerin potency in each sample.

Nitroglycerin potency as a function of time in samples taken as described from the commercial IV sets is set forth in Table 3.

TABLE 3

Nitroglycerin Potency Delivered Out of Commercial Infusion Sets (1 ml/min) As A Function of Time.
Nominal Concentration In Glass IV Bottle 100 μg/ml.
Nitroglycerin Potency
(μg/ml)

| | IV Set | | | | | | | |
| --- | --- | --- | --- | --- | --- | --- | --- | --- |
| | Travenol A | McGaw B | Cutter C | Abbott D | Baxter E | Avon A-10 F | Avon A-11 G | Braun H |
| Time (minutes) | | | | | IV Bottle | | | |
| | 93.4 | 94.7 | 97.0 | 95.7 | 102.0 | 95.1 | 94.6 | 93.2 |
| Initial | 72.8 | 71.4 | 69.7 | 58.9 | 79.8 | 81.8 | 76.7 | 63.3 |
| 10 | 63.2 | 58.5 | 57.4 | 46.0 | 71.1 | 67.4 | 63.3 | 55.0 |
| 20 | 70.7 | 58.8 | 52.5 | 44.8 | 73.1 | 63.0 | 55.2 | 60.2 |
| 30 | 72.6 | 64.1 | 55.7 | 49.1 | 72.2 | 62.0 | 55.5 | 66.8 |
| 45 | 76.6 | 62.3 | 66.5 | 52.8 | 77.5 | 63.9 | 56.4 | 70.4 |
| 60 | 78.5 | 65.7 | 64.9 | 56.8 | 79.1 | 68.5 | 69.7 | 75.6 |
| 120 | 83.2 | 72.9 | 69.7 | 58.9 | 87.8 | 79.8 | 73.5 | 75.0 |

The four sets sold primarily in the United States (Travenol, McGaw, Cutter, Abbott) and the four sets sold primarily in Europe (Taxter, Avon A-10, Intrafix ® Air Inf. Set, Avon A-11) are tested under essentially the same conditions. As seen in Table 3, significant losses in the potency of nitroglycerin admixture solutions are seen when such admixture solutions are delivered through all eight infusion sets tested in a manner designed to simulate a clinical setting.

While the degree of potency loss varies from set to set, the pattern of loss is consistent among them with a maximum loss occurring at 10 to 20 minutes after initiation. The differences in potency loss among sets can be attributed to several factors: (1) the type of plastic used to construct the set, (2) the length of the set, (3) the flow rate of the set, and (4) the set-up time required for each different set design.

It should be recognized that the total volume of the admixture is assumed to be 250 ml. but actual volumes may deviate from that. Significant variance in fill volumes of the intravenous solutions as received from the manufacturer can account for the range of initial potencies seen.

It should also be noted that there is a lag time period, ranging from about 3.5 minutes to 9 minutes, from the time of initial plastic/nitroglycerin contact to the time of the first (initial) sample from each of the sets, due to the filling and regulating periods needed. This also helps to explain the lower than anticipated initial potencies observed.

The type of plastic used in each set is not known but it is believed that none utilize polyolefin drip tubes. For the processes of adsorption/persorption, the extent of nitroglycerin loss is directly related to the surface area in contact with the nitroglycerin solution. The sets of Table 3 are employed as received, and thus the length and diameters (i.e. surface areas) are uncontrolled variables. Similarly, the length of time the surface is in contact with the solution would be expected to directly effect nitroglycerin potency loss. While effort is made to set uniform flow rates, variations in the flow rate are unavoidable. Finally, the time of the initial filling of the sets vary by up to several minutes. This may result in changes in the time to peak potency loss.

EXAMPLE II

Nitroglycerin Loss Through IV Sets with Polyolefin Drip Tubes

Using procedures substantially similar to those described in Example I, nitrogycerin potency loss is determined in IV fluid samples run through a conventional IV infusion set having a polyolefin drip tube. The drip tube employed is a commercially-available coextruded tubing having an inner liner of low density polyethylene and an outside cover of poly-ethyl-vinyl alcohol.

Table 4 sets forth the results of such testing, providing the nitroglycerin potency measurement as a percentage of the nitroglycerin potency in the IV bottle. Such percentage values represent averages of several experimental runs.

TABLE 4

| Nitroglycerin Potency in Samples Delivered from an IV Set With Polyolefin Drip Tube as a Function of Time | |
|---|---|
| Time (Minutes) | Amount of Nitroglycerin in Sample (% of Concentration in IV Bottle) |
| Initial | 95.7% |
| 30 | 96.7% |
| 60 | 97.0% |
| 120 | 94.5% |
| 240 | 95.8% |
| 1440 | 97.1% |

The slight decrease in potency is probably attributable to the polyvinylchloride drip chamber employed in the IV set utilized for testing.

The Table 4 data demonstrate the polyethylene lined drip tubing can minimize the loss of nitroglycerin in IV fluid infused through a conventional IV set.

What is claimed is:

1. In an intravenous infusion set suitable for the parenteral administration of nitroglycerin solutions, said intravenous infusion set comprising a reservoir of nitroglycerin solution, a flexible drip tube connecting said nitroglycerin solution reservoir to an administration needle, said drip tube having flow control means positioned in the drip tube flow path between said reservoir and said needle, the improvement which comprises constructing the inner surface of said flexible drip tube essentially of a polyolefin plastic material.

2. An intravenous infusion set according to claim 1 wherein the polyolefin inner surface of the drip tube is selected from polyethylene having a molecular weight of from about 1,500 to 150,000 and polypropylene.

3. An intravenous infusion set according to claim 2 wherein the polyolefin inner surface of the drip tube is low to intermediate density polyethylene.

4. An intravenous infusion set according to claim 2 wherein the polyolefin inner surface of the drip tube is high density polyethylene.

5. An intravenous infusion set according to claims 1, 2, 3 or 4 wherein the drip tube is constructed essentially entirely of the polyolefin material.

6. An intravenous infusion set according to claim 1, 2, 3 or 4 wherein the drip tube has an inner lining of the polyolefin material and an outer lining of a non-polyolefin material.

7. A method for parenterally administering a nitroglycerin solution to a patient with minimized loss of nitroglycerin potency during parenteral infusion, said method comprising passing said nitroglycerin solution through a flexible drip tube to an intravenous administration needle for infusion, said flexible drip tube having its inner surface constructed essentially of a polyolefin plastic material.

8. A method according to claim 7 wherein the polyolefin inner surface of the drip tube is selected from polyethylene having a molecular weight of from about 1,500 to 150,000 and polypropylene.

9. A method according to claim 8 wherein the polyolefin inner surface of the drip tube is essentially low to intermediate density polyethylene.

10. A method according to claim 8 wherein the polyolefin inner surface of the drip tube is essentially high density polyethylene.

11. A method according to claim 7 wherein said nitroglycerin solution passes through said flexible drip tube at a rate of from about 0.2 ml/min to 2.0 ml/min.

12. A method according to claims 7, 8, 9, 10 or 11 wherein the drip tube is constructed essentially entirely of the polyolefin material.

13. A method according to claims 7, 8, 9, 10 or 11 wherein the drip tube has an inner lining of the polyolefin material and an outer lining of a non-polyolefin material.

14. An intravenous infusion set package comprising:
(A) a flexible drip tube suitable for parenterally administering a nitroglycerin solution through an administration needle connected to said drip tube, said drip tube having flow control means positioned in the flow path thereof and an inner surface constructed essentially of a polyolefin plastic material; and
(B) one or more nitroglycerin ampules containing sufficient amounts of nitroglycerin suitable for preparing a nitroglycerin solution to be parenterally administered through said drip tube and administration needle.

15. An intravenous infusion set package according to claim 14 wherein the polyolefin inner surface of the drip tube is selected from polyethylene having a molecular weight of from about 1,500 to 150,000 and polypropylene.

16. An intravenous infusion set package according to claim 15 wherein the polyolefin inner surface of the drip tube is low to intermediate density polyethylene.

17. An intravenous infusion set according to claim 15 wherein the polyolefin inner surface of the drip tube is high density polyethylene.

18. An intravenous infusion set package according to claims 14, 15, 16 or 17 wherein the drip tube is constructed essentially entirely of the polyolefin material.

19. An intravenous infusion set package according to claim 14, 15, 16 or 17 wherein the drip tube has an inner lining of the polyolefin material and an outer lining of a non-polyolefin material.

* * * * *